(12) United States Patent
Yu et al.

(10) Patent No.: US 6,743,617 B1
(45) Date of Patent: Jun. 1, 2004

(54) HUMAN LYSOZYME GENE, ITS ENCODED POLYPEPTIDE AND THE METHOD FOR PREPARING THEM

(75) Inventors: Long Yu, Institute of Genetics, Fudan University, Shanghai (CN); Qiang Fu, Shanghai (CN); Yong Zhao, Shanghai (CN); Honglai Zhang, Shangahi (CN); Anding Bi, Shanghai (CN)

(73) Assignee: Long Yu, Shanghai (CN)

( * ) Notice: Subject to any disclaimer, the term of this patent is extended or adjusted under 35 U.S.C. 154(b) by 0 days.

(21) Appl. No.: 09/786,024

(22) PCT Filed: Aug. 30, 1999

(86) PCT No.: PCT/CN99/00132

§ 371 (c)(1),
(2), (4) Date: Jul. 5, 2001

(87) PCT Pub. No.: WO00/12723

PCT Pub. Date: Mar. 9, 2000

(30) Foreign Application Priority Data

Aug. 31, 1998 (CN) ......................... 98111041 A

(51) Int. Cl.⁷ ................................. C12N 4/36
(52) U.S. Cl. .................... 435/206; 435/183; 435/195; 435/252.3; 435/252.33; 435/255.1; 435/320.1; 536/23.2
(58) Field of Search ................. 435/183, 195, 435/206, 252.3, 252.33, 255.1, 320.1; 536/23.2

(56) References Cited

U.S. PATENT DOCUMENTS 5,643,758 A * 7/1997 Guan et al. ................ 435/69.7

OTHER PUBLICATIONS

Hiller et al. Accession AA398583. Aug. 12, 1997.*
de Baetselier et al. Accession AAR05721. Aug. 16, 1990 (Alignment No. 1).*
de Baetselier et al. Accession AAR057521. Aug. 16, 1990 (Alignment No. 1).*
Jung et al. Accession V00428. Sep. 12, 1993 (Alignment No. 2).*
Online clipping from Entrez–PubMed, Messier W.S., "Episodic adaptive evolution of primate lysozymes", *Nature*, (6612), pp. 151–154, Jan. 1997.
Online clipping from Entrez–PubMed, Sippel et al., "Cloning of chicken lysozyme structural gene sequences synthesized in vitro", *Nucleic Acids Res*, pp. 3275–3294, 1978.
Sava et al., "Lysozyme and Cancer: Role of Exogenous Lysozyme as Anticancer Agent (Review)", *Anticancer Research*, vol. 9, pp. 583–592, 1989.
"The Chemistry of Lysozyme and its use as a food preservative and a pharmaceutical", *Critical Review Food Science Nutrition*, vol. 26, issue 4, pp. 359–395, 1988.
Printout of various abstracts, including those herein.
Printout from NCBI Sequence Viewer regarding AC003687, Bireen et al., "*Homo sapiens* chromosome 17, clone HRPC29G21, complete sequence", 1998.
Printout from NCBI Sequence Viewer regarding M25446, Sippel et al., "Chicken lysozyme mRNA, partial cds", 1993.
Printout from NCBI Sequence Viewer regarding P07232, Swanson et al., "Lysozyme C. Presursor (1, 4–Beta–N–Acetylmuramidase Cy", Jul. 1998.
Printout from NCBI Sequence Viewer regarding P79847, Messier et al., "Lysozyme C Precursor (1, 4–Beta–N–Acetylmuramidase C)", *Nature* 385, pp. 151–154 Nov. 1997 (above).

* cited by examiner

*Primary Examiner*—Ponnathapu Achutamurthy
*Assistant Examiner*—Christian L. Fronda
(74) *Attorney, Agent, or Firm*—Baker Botts L.L.P.

(57) ABSTRACT

The invention relates to a novel member LYC3 of lysozyme gene family. The invention provides the cDNA sequence encoding for the novel lysozyme, the polypeptide encoded by the sequence, as well as the method for producing said novel human lysozyme utilizing recombinant technology. The invention also provides the use of the novel human lysozyme.

9 Claims, 2 Drawing Sheets

```
             10        20        30        40        50        60
LYC3       MLLALVCLLSCLLPSSEAKLYGRCELARVLHDFGLDGYRGYSLADWVCLAYFTSGFNAAA
            : ..   :    : ...:..  ::::::..:. .:::::.: :::..::::: .  :::.:.  :
gi|1790947 MRALIILGLVLLSVTVQGKIFERCELARTLKKLGLDGYKGVSLANWVCLAKWESGYNTEA
             10        20        30        40        50        60

70        80        90       100       110
LYC3       LDYE-ADGSTNNGIFQINSRRWCSN-LTPNVPNVCRMYCSDLLNPNLKDTVICAMKITQE
            .:.. .:  :::  ::::::::: ::..:   :::..   ...:..  ::  ::.  :. :.  :: ::.....
gi|1790947 TNYNPGDESTDYGIFQINSRYWCNNGKTPGAVDACHISCSALLQNNIADAVACAKRVVSD
              70        80        90       100       110       120

120       130       140
LYC3       PQGLGYWEAWRHHCQGKDLTEWVDGCDF
            :::.    :  ::::.,:::.::....:  ::
gi|1790947 PQGIRAWVAWRNHCQNKDVSQYVKGCGV
              130       140
```

Fig. 1A

```
             10        20        30        40        50
LYC3       MLLALVCLLSCLLP-SSEAKLYGRCELARVLHDFGLDGYRGYSLADWVCLAYFTSGFNAA
            :   :.  .:  :.:: ..  .:.:::::::  ...  .:::.::::::..::: :  :  :.::..
sp|O0702   MRSLLILVL-CFLPLAAPGKVYGRCELAAAMKRMGLDNYRGYSLGNWVCAAKFESNFNTG
             10        20        30        40        50

60        70        80        90       100       110
LYC3       ALDYEADGSTNNGIFQINSRRWCSN-LTPNVPNVCRMYCSDLLNPNLKDTVICAMKITQE
            :  .  ..:::.  .::.:::::  :..   ::.   :.:..  :: ::.  ..  .: :: :....
sp|O0702   ATNRNTDGSTDYGILQINSRWWCNDGRTPGSKNLCHIPCSALLSSDITASVNCAKKIVSD
              60        70        80        90       100       110

120       130       140
LYC3       PQGLGYWEAWRHHCQGKDLTEWVDGCDF
            .:..   :  :::.::.:   :... :.    :: .
sp|O0702   GNGMNAWVAWRKHCKGTDVNVWIRGCRL
              120       130       140
```

Fig. 1B

HUMAN LYSOZYME GENE, ITS ENCODED POLYPEPTIDE AND THE METHOD FOR PREPARING THEM

This application is a National Stage application under 35 U.S.C. § 371 of International Application Serial No. PCT/CN99/00132 filed Aug. 30, 1999 and published in Chinese as WO 00/12723 on Mar. 9, 2000, which claims priority to Chinese Application Serial No. 98111041.X, filed Aug. 31, 1998.

FIELD OF INVENTION

The invention relates to a new polynucleotide, the polypeptide encoded by said polynucleotide, the uses of said polynucleotide and polypeptide, and the methods for preparing same. In particular, the polypeptide of the invention is identified as a new member of the lysozyme family.

PRIOR ART

Lysozyme exists ubiquitously in all parts of organisms, including various tissues, organs, and sera; it is especially abundant in egg white. Lysozyme is mainly secreted by the epithelial cell of certain glands and some kinds of leukocyte.

Lysozyme was first reported by Fleming, et al. in 1922. Afterward, lysozyme has been widely studied. A lot of papers concerning its crystal structure, protein catalytic domains, catalytic dynamics, immunology, molecular evolutionary, and so on, have been published. Lysozyme is one of the proteins that are studied most extensively and intensively. However, the study on lysozyme gene is not yet sufficient. Nowadays, only a few lysozyme genes from different species, such as *E.coli* T4, salmonella P22 phage, bacillus φ phage and chicken, etc., have been cloned. (1983 J. Mol. Biol. 165. 229–248; 1985 Virology 143, 280–289; 1987 Proc. Natl. Acad. Sci. USA, 77, 5759–5763). The cloning about human lysozyme gene was also reported (1988, Gene 66,223–234).

The main function of lysozyme is to hydrolyze the beta(1–4) glycosidic bond between N-acetylmuramic acid (NAM) and N-acetylgluconic acid (NAG) of the bacterial cell wall. In the organism, lysozyme can act as a nonspecific immune molecule against bacterial infections, and as a digestive enzyme in enteron and some mollusks which live on bacteria. Further, lysozyme has the function of inhibiting tumor growth. Therefore, lysozyme has important applications in both industry and medicine.

SUMMARY OF INVENTION

One purpose of the invention is to provide a new polynucleotide which encodes a new member of lysozyme gene family. The new human lysozyme is named LYC3.

Another purpose of the invention is to provide a new member of lysozyme protein family, which is named LYC3.

Still another purpose of the invention is to provide a new method for preparing said new human lysozyme by recombinant techniques.

The invention also relates to the uses of said human lysozyme and its coding sequence.

In one aspect, the invention provides an isolated DNA molecule, which comprises a nucleotide sequence encoding a polypeptide having human LYC3 protein activity, wherein said nucleotide sequence shares at least 70% homology to the nucleotide sequence of nucleotides 81–521 in SEQ ID NO: 3, or said nucleotide sequence can hybridize to the nucleotide sequence of nucleotides 81–521 in SEQ ID NO: 3 under moderate stringency. Preferably, said nucleotide sequence encodes a polypeptide comprising the amino acid sequence of SEQ ID NO: 4 or of amino acids 19–146 of SEQ ID NO: 4. More preferably, the sequence comprises the nucleotide sequence of nucleotides 81–521 in SEQ ID NO: 3.

Further, the invention provides an isolated LYC3 polypeptide, which comprises a polypeptide having the amino acid sequence of SEQ ID NO: 4 or of amino acids 19–146 of SEQ ID NO: 4, its active fragments, and its active derivatives. Preferably, the polypeptide is a polypeptide having the amino acid sequence of SEQ ID NO: 4.

The invention also provides a vector comprising said isolated DNA.

The invention further provides a host cell transformed with said vector.

In another aspect, the invention provides a method for producing a polypeptide with the activity of LYC3 protein, which comprises:

(a) forming an expression vector of LYC3 protein comprising the nucleotide sequence encoding the polypeptide having the activity of LYC3 protein, wherein said nucleotide sequence is operably linked with an expression regulatory sequences, and said nucleotide sequence shares at least 70% homology to the nucleotide sequence of positions 81–521 in SEQ ID NO: 3;

(b) introducing the vector of step (a) into a host cell, thereby forming a recombinant cell of LYC3 protein;

(c) culturing the recombinant cell of step (b) under the conditions suitable for the expression of LYC3 polypeptides;

(d) isolating the polypeptides having the activity of LYC3 protein.

In one embodiment of the present invention, the isolated polynucleotide has a full length of 544 nucleotides, whose detailed sequence is shown in SEQ ID NO: 3. The open reading frame (ORF) locates at nucleotides 81–521.

In the present invention, the term "isolated" or "purified" or "substantially pure" DNA refers to a DNA or fragment which has been isolated from the sequences which frank it in a naturally occurring state. The term also applied to DNA or DNA fragment which has been isolated from other components naturally accompanying the nucleic acid and from proteins naturally accompanying it in the cell.

In the present invention, the term "LYC3 protein encoding sequence" or "LYC3 polypeptide encoding sequence" refers to a nucleotide sequence encoding a polypeptide having the activity of LYC3 protein, such as the nucleotide sequence of positions 81–521 in SEQ ID NO: 3 or its degenerate sequence. The degenerate sequences refer to the sequences formed by replacing one or more codons in the ORF of 81–521 in SEQ ID NO: 3 with degenerate codes which encode the same amino acid. Because of the degeneracy of codon, the sequence having a homology as low as about 70% to the sequence of nucleotides 81–521 in SEQ ID NO: 3 can also encode the sequence shown in SEQ ID NO: 4. The term also refers to the nucleotide sequences that hybridize with the nucleotide sequence of nucleotides 81–521 in SEQ ID NO: 3 under moderate stringency or preferably under high stringency. In addition, the term also refers to the sequences having a homology at least 70%, preferably 80%, more preferably 90% to the nucleotide sequence of nucleotides 81–521 in SEQ ID NO: 3. Moreover, the term includes a nucleotide sequence encoding a mature protein without signal peptide, such as the nucleotide sequence of position 135–521 in SEQ ID NO: 3.

The term also refers to variants of the sequence in SEQ ID NO: 3, which are capable of coding for a protein having the same function as human LYC3 protein. These variants includes, but are not limited to: deletions, insertions and/or substitutions of several nucleotides (typically 1–90, preferably 1–60, more preferably 1–20, and most preferably 1–10) and additions of several nucleotides (typically less than 60, preferably 30, more preferably 10, most preferably 5) at 5' end and/or 3' end.

In the present invention, "substantially pure" proteins or polypeptides refers to those which occupy at least 20%, preferably at least 50%, more preferably at least 80%, most preferably at least 90% of the total sample material (by wet weight or dry weight). Purity can be measured by any appropriate method, e.g., in the case of polypeptides by column chromatography, PAGE or HPLC analysis. A substantially purified polypeptides is essentially free of naturally associated components.

In the present invention, the term "LYC3 polypeptide" or "LYC3 protein" refers to a polypeptide having the activity of LYC3 protein comprising the amino acid sequence of SEQ ID NO: 4 or of amino acids 19–146 of SEQ ID NO: 4. The term also comprises the variants of said amino acid sequence which have the same function of human lysozyme. These variants include, but are not limited to, deletions, insertions and/or substitutions of several amino acids (typically 1–50, preferably 1–30, more preferably 1–20, most preferably 1–10), and addition of one or more amino acids (typically less than 20, preferably less than 10, more preferably less than 5) at C-terminal and/or N-terminal. For example, the protein function are usually unchanged when an amino residue is substituted by a similar or analogous one. Further, the addition of one or several amino acids at C-terminal and/or N-terminal will not change the function of protein. The term also includes the active fragments and derivatives of LYC3 protein.

The variants of polypeptide include homologous sequences, allelic variants, natural mutants, induced mutants, proteins encoded by DNA which hybridizes to LYC3 DNA under high or low stringency conditions as well as the polypeptides or proteins retrieved by antisera raised against LYC3 polypeptide. The present invention also provides other polypeptides, e.g., fusion proteins, which include the LYC3 polypeptide or fragments thereof. In addition to substantially full-length polypeptide, the soluble fragments of LYC3 polypeptide are also provided. Generally, these fragments comprise at least 10, typically at least 30, preferably at least 50, more preferably at least 80, most preferably at least 100 consecutive amino acids of human LYC3 polypeptide.

The present invention also provides the analogues of LYC3 protein or polypeptide. Analogues can differ from naturally occurring LYC3 polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo, or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences which have phosphorylated amino acid residues, e.g., phosphotyrosine, phosphoserine, phosphothronine, as well as sequences which have been modified to improve their resistance to proteolytic degradation or to optimize solubility properties.

The invention also includes antisense sequence of the sequence encoding LYC3 polypeptide. Said antisense sequence can be used to inhibit expression of LYC3 in cells.

The invention also include probes, typically having 8–100, preferably 15–50 consecutive nucleotides. These probes can be used to detect the presence of nucleic acid molecules coding for LYC3 in samples.

The present invention also includes methods for detecting LYC3 nucleotide sequences, which comprises hybridizing said probes to samples, and detecting the binding of the probes. Preferably, the samples are products of PCR amplification. The primers in PCR amplification correspond to coding sequence of LYC3 polypeptide and are located at both ends or in the middle of the coding sequence. In general, the length of the primers is 20 to 50 nucleotides.

A variety of vectors known in the art, such as those commercially available, are useful in the invention.

In the invention, the term "host cells" includes prokaryotic and eukaryotic cells. The common prokaryotic host cells include *Escherichi coli, Bacillus subtilis*, and so on. The common eukaryotic host cells include yeast cells, insect cells, and mammalian cells. Preferably, the host cells are eukaryotic cells, e.g., CHO cells, COS cells, and the like.

In another aspect, the invention also includes antibodies, preferably monoclonal antibodies, which are specific for polypeptides encoded by LYC3 DNA or fragments thereof. By "specificity" is meant an antibody which binds to the LYC3 gene products or a fragments thereof. Preferably, the antibody binds to the LYC3 gene products or a fragments thereof and does not substantially recognize and bind to other antigenically unrelated molecules. Antibodies which bind to LYC3 and block LYC3 protein and those which do not affect the LYC3 function are included in the invention. The invention also includes antibodies which bind to the LYC3 gene product in its unmodified as well as modified form.

The present invention includes not only intact monoclonal or polyclonal antibodies, but also immunologically-active antibody fragments, e.g., a Fab' or (Fab)$_2$ fragment, an antibody light chain, an antibody heavy chain, a genetically engineered single chain Fv molecule (Lander, et al., U.S. Pat. No. 4,946,778), or a chimeric antibody, e.g., an antibody which contains the binding specificity of a murine antibody, but the remaining portion of which is of human origin.

The antibodies in the present invention can be prepared by various techniques known to those skilled in the art. For example, purified LYC3 gene products, or its antigenic fragments can be administrated to animals to induce the production of polyclonal antibodies. Similarly, cells expressing LYC3 or its antigenic fragments can be used to immunize animals to produce antibodies. Antibodies of the invention can be monoclonal antibodies which can be prepared by using hybridoma technique (See Kohler, et al., Nature, 256; 495,1975; Kohler, et al., Eur. J. Immunol. 6: 511,1976; Kohler, et al., Eur. J. Immunol. 6: 292, 1976;

Hammerling, et al., In Monoclonal Antibodies and T Cell Hybridomas, Elsevier, N.Y., 1981). Antibodies of the invention comprise those which block LYC3 function and those which do not affect LYC3 function. Antibodies in the invention can be produced by routine immunology techniques and using fragments or functional regions of LYC3 gene product. These fragments and functional regions can be prepared by recombinant methods or synthesized by a polypeptide synthesizer. Antibodies binding to unmodified LYC3 gene product can be produced by immunizing animals with gene products produced by prokaryotic cells (e.g., E. coli); antibodies binding to post-translationally modified forms thereof can be acquired by immunizing animals with gene products produced by eukaryotic cells (e.g., yeast or insect cells).

The full length human LYC3 nucleotide sequence or its fragment of the invention can be prepared by PCR amplification, recombinant method and synthetic method. For PCR amplification, one can obtain said sequences by designing primers based on the nucleotide sequence disclosed in the invention, especially the sequence of ORF, and using cDNA library commercially available or prepared by routine techniques known in the art as a template. When the sequence is long, it is usually necessary to perform two or more PCR amplifications and link the amplified fragments together in the correct order.

Once the sequence is obtained, a great amount of the sequences can be produced by recombinant methods. Usually, said sequence is cloned in a vector which is transformed into a host cell. Then the sequence is isolated from the amplified host cells using conventional techniques.

In addition to recombinant techniques, the protein fragments of the invention may also be prepared by direct chemical synthesis using solid phase synthesis techniques (Stewart et al., (1969) Solid-Phase Peptide Synthesis, WH Freeman Co., San Francisco; Merrifield J. (1963), J. Am. Chem. Assoc. 85: 2149–2154). In vitro protein synthesis can be performed manually or automatically, e.g., using a Model 431 Peptide Synthesizer (Applied Biosystems, Foster City, Calif.). The fragments of protein of the invention can be synthesized separately and linked together using chemical methods so as to produce full-length molecule.

The sequences encoding the protein of the present invention are also valuable for gene mapping. For example, the accurate chromosome mapping can be performed by hybridizing cDNA clones to a chromosome in metaphase. This technique can use cDNA as short as about 500 bp, or as long as about 2000 bp, or more. For details, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found in, e.g., Mendelian Inheritance in Man (available on-line through Johns Hopkins University Welch Medical Library). The relationships between genes and diseases that have been mapped to the same chromosomal region are then identified through linkage analysis.

Then, the differences in the cDNA or genomic sequence between affected and unaffected individuals can also be determined. If a mutation is observed in some or all of the affected individuals but not in any normal individual, then the mutation is likely to be the causative agent of the disease.

The substances which act with the LYC3, e.g., receptors, inhibitors and antagonists, can be screened out by various conventional techniques and using the protein of the invention.

The protein, antibody, inhibitor, antagonist or receptor of the invention provide different effects when administered in therapy. Usually, these substances are formulated with a non-toxic, inert and pharmaceutically acceptable aqueous carrier. The pH typically ranges from 5 to 8, preferably about 6–8, although pH may alter according to the property of the formulated substances and the diseases to be treated. The formulated pharmaceutical composition is administered in conventional routine including, but not be limited to, intramuscular, intraperitoneal, subcutaneous, intracutaneous, or topical administration.

As an example, the human LYC3 protein of the invention may be administrated together with the suitable and pharmaceutically acceptable carrier. The examples of carriers include, but are not limited to, saline, buffer solution, glucose, water, glycerin, or the combination thereof. The pharmaceutical formulation should be suitable for the delivery method. The human LYC3 protein of the invention may be in the form of injections which are made by conventional methods and using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., from about 1 ug to 5 mg per kg body weight per day. Moreover, the polypeptide of the invention can be administrated together with other therapeutic agent.

When the human LYC3 polypeptides of the invention are used as a pharmaceutical, the therapeutically effective amount of the polypeptides are administrated to mammals. Typically, the therapeutically effective amount is at least about 10 ug/kg body weight and less than about 8 mg/kg body weight in most cases, and preferably about 10 ug–1 mg/kg body weight. Of course, the precise amount will depend upon the factors, such as delivery methods, the subject health, and the like, and is within the judgment of the skilled clinician.

In one embodiment, the polynucleotide of the invention is 544 bp in full length whose detailed sequence is shown in SEQ ID NO: 3 with the ORF located at positions 81–521. Said polynucleotide was obtained as follows: human brain gt 11 cDNA library (Clontech) was used as a template and PCR was carried out with the synthetic forward primer A1 5'-AGAGTGGTGGTGGCTCCACTCTG-3' (SEQ ID NO. 1) and reverse primer B : 5'-TGCTGTGCATGGTTCCGTC CATC-3' (SEQ ID NO. 2). A target fragment of 544 bp was obtained. The sequencing of the PCR product gave the full length cDNA sequence shown in SEQ ID NO:3.

Homology comparison showed that the nucleotide sequence and the coded protein sequence of the invention shared remarkable homology to other lysozymes from different origins. Therefore, it indicates it is a new member of lysozyme family and has some important functions of the family.

Lysozyme can lyse cells by hydrolyze the beta(1–4) glycosidic bond between N-acetylmuramic acid (NAM) and N-acetylgluconic acid (NAG) of the bacterial cell wall. In the organisms, lysozyme can act as a nonspecific immune molecule against bacterial infections, and as a digestive enzyme in enteron and some mollusks which live on bacteria. Further, lysozyme has the function of inhibiting tumor growth. In 1955, Caselli and Shumacher (Boll Ocul 34:513–533, 1955) reported on the lysozyme-mediated 70% inhibition of neoplastic transformation in cornea of chicken infected by Rous sarcoma virus. Many other experiments indicated that lysozyme participates in the process of tumor diffusion and interacts with phospho- and glucolipid molecule of tumor cells. The inhibition effect on human tumor of lysozyme was reported and patented (1980 Jpn Kokai, Tokkyo Koho 33,409; 1980 Jpn Kokai Tokkyo Koho 33,408). As to the mechanism of lysozyme inhibition on tumor, there are two possibilities: (1) lysozyme directly activates the organism's immunity functions; (2) lysozyme indirectly enhances the organism's immune ability (1989 Anticancer Research 9, 583–592).

DESCRIPTION OF DRAWINGS

FIG. 1 shows an alignment comparison of amino acid sequences of human LYC3 and other lysozymes. FIG. 1A shows a homology comparison of amino acid sequences of human LYC3 (SEQ ID NO. 4) and lysozyme C of *Trachypithecus francoisi* (gi|1790947)(SEQ ID NO. 11). FIG. 1B shows a homology comparison of amino acid sequences of human LYC3 (SEQ ID NO. 4) and lysozyme C of ring-necked pheasant (sp|p00702)(SEQ ID NO. 12). The identical amino acids are indicated by ":" between the sequences, and the similar amino acids indicated by ".". The similar amino acids are as follows: A,S,T; D,E; N,Q; R,K; I,L,M,V; F,Y,W.

Figure 2:
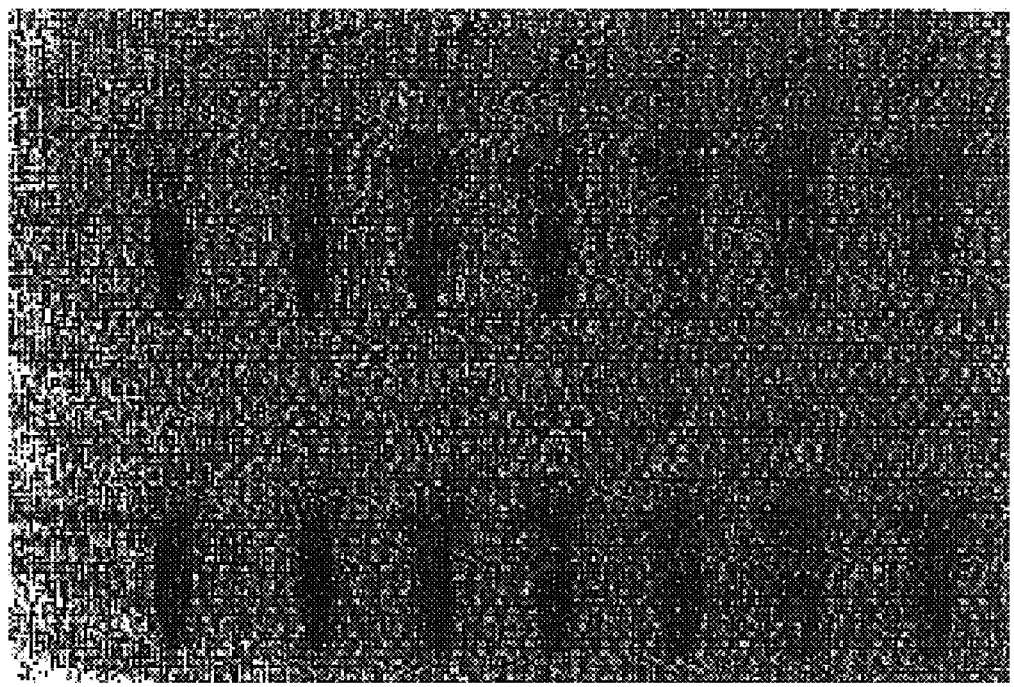
FIG. 2 shows the bacteriolysis effect of LYC3 of the invention.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLES

Example 1
The Cloning and Sequencing of LYC3 cDNA Sequence

1. Amplification With Primers

The template was human brain λ gt 11 cDNA library (commercially available from Clontech). PCR with forward primer A1: 5'-AGAGTGGTGGTGGCTCCACTCTG-3' (SEQ ID NO: 1) and reverse primer B: 5'-TGCTGTGCATGGTTCCGTCCATC-3' (SEQ ID NO: 2) was carried out. The PCR condition for A1/B was 4 mins at 93° C.; followed by 35 cycles with 1 min at 93° C., 1 min at 69° C., and 1 min at 72° C.; and, finally 5 mins at 72° C. The PCR fragments were detected by electrophoresis. The target fragment was 544 bp.

2. Sequencing PCR Products

The obtained PCR products were linked with pGEM-T® vector (Promega) and transformed into *E. coli* JM103. The plasmids were extracted using QIAprep Plasmid Kit (QIAGEN). The oriented serial deletion of the inserted fragments was carried out with Double-Stranded Nested Deletion Kit (Pharmacia), and the deletants were quickly identified by PCR and arranged in order. The deletants successively cut-off were sequenced with SequiTherm EXCEL™ DNA Sequencing Kit (Epicentre Technologies). A full length cDNA sequence of 544 bp was obtained by overlapping the sequences with computer software. The detailed sequence is shown in SEQ ID NO: 3 with an open reading frame (ORF) located at nucleotides 81–521.

According to the resultant full-length cDNA sequence, the amino acid sequence of LYC3 was deduced, having 146 amino acid residues totally. See SEQ ID NO: 4 for its amino acid sequence in details.

Example 2
Homologous Comparison

The full length cDNA sequence of LYC3 and the coded protein were used for homologous screening Non-redundant GenBank+EMBL+DDBJ+PDB and GenBank CDS translations+PDB+SwissProt+Spupdate+PIR databases by BLAST algorithm. The result showed that they shared high homology to other members of the lysozyme family. The amino acid sequence of LYC3 shares 51.4% identity and 64.4% similarity with *Trachypithecus francoisi* lysozyme C (gi|1790947) (FIG. 1A), and 46.6% identity and 59.2% similarity with lysozyme C of ring-necked pheasant (sp|p00702)(FIG. 1B), when analyzed by PCGENE software.

In particular, in amino acid sequence of LYC3, there exists a 19 amino acids signature sequence of lysozyme and alpha-lactoalbumin: $CX_3CX_2(L/M/F)X_3(D/E/N)(L/I)X_5C$ (SEQ ID NO. 10) [Note: In the sequence, X represents any amino acid, digits such as "2" denote the number of amino acid, "(L/M/H)" represents any of these three amino acids]. Lysozyme and alpha-lactoalbumin are two proteins related closely in evolution (Eur. J. Biochem. 182: 111–118). In the protein of the present invention, the sequence matching the signature is: CRMYCSDLLNPNLKDTVIC (residues 93–111 in SEQ ID NO: 4). It indicates that the LYC3 of the present invention belongs to lysozyme family, and has the relative functions of the lysozyme family.

The human LYC3 protein has a signal peptide of 18 amino acids (residues 1–18 of SEQ ID NO: 4). After cleavage of the signal peptide, the mature human LYC3 protein has the amino acid sequence of residues 19–146 of SEQ ID NO: 4.

Lysozyme can lyse cells by hydrolyze the beta(1–4) glycosidic bond between N-acetylmuramic acid (NAM) and N-acetylgluconic acid (NAG) of the bacterial cell wall. In the organisms, lysozyme can act as a nonspecific immune molecule against bacterial infections, and as a digestive enzyme in enteron and some mollusks which live on bacteria.

Lysozyme has important applications in both industry and medicine.

First, in industry (mainly in food industry), lysozyme can be used as a preservative or additive for food. In this respect, the Japanese have developed many use of lysozyme and owe many patents. For example, they use lysozyme as a preservative for fresh fruit, vegetable, soybean milk, marine foods and meat. Lysozyme can also be used as an additive for infant's foods to simulate human milk (1988, Crit Rev Food Sci Nutr 26(4):359–395).

In respect of pharmaceutical use, lysozyme can be used to cure viral and bacterial infections. For example, EDTA-tris-lysozyme solutions are effective on the pseudomonas cystitis induced by *E.coli* infection. Lysozyme concentration in human and animal serum is an indicator of infection. Zajaczkowska-Bialowas and Murai studied the relationship between lysozyme activity in saliva and diseases of oral cavity. The result showed that lysozyme had obvious alleviation effect on the symptom of chronic periodontitis. Besides, they found the synergistic effects of lysozyme and some antibiotics. When lysozyme was used alone, even in a large amount, the bacteriolysis effect on *S. aureus* was little. But with the presence of amoxicillin, the lysis effect was enhanced and in proportion to the amount of lysozyme (1988 Crit Rev Food Sci Nutr 26(4):359–395).

Further, lysozyme has the function of inhibiting tumor growth. In 1955, Caselli and Shumacher (1955, Boll Ocul 34:513–533) reported on the lysozyme-mediated 70% inhibition of neoplastic transformation in cornea of chicken infected by Rous sarcoma virus. Many other experiments indicated that lysozyme had some relationship to the inhibition of tumor diffusion (1988 Clin. Expl. Metastasis 6:245–253; 1998 Folia Onclo 10, Suppl A: 219–224; 1988 Eur. J. Cancer Clin. Onco. 124:1737–1743). It is also found that lysozyme interacts with phospho- and glucolipid molecule of tumor cells. The lysozyme's inhibition effect on human tumor was reported. Laterza successfully cured a case of small intestine reticulation sarcoma with diffusion after operation and radiotherapy ("Atti del II Simposium Internazionale sul Lisozima", Milano. 7–8–9 1961. Vol I, sez V, pp 49–50). Battaglia et al. found that, though lysozyme could not reduce the volume of tumor, it had distinct effects of pain-killing and helping recovery in curing carcinomas of stomach, prostate, uterus and mammary gland ("Atti del II Simposium Internazionale sul Lisozima di Fleming", Milano. 34–5 1964. Vol I, sez IV, pp 69–76). In Japan, the application of lysozyme in curing cancer was patented (1980 Jpn Kokai Tokkyo Koho 33, 409; 1980 Jpn Kokai Tokkyo Koho 33,408). Besides, A. Vacca et al. in 1985 reported an attempt of curing multiple mycloma by chemoimmunology with oral lysozyme as an immunomodulating agent. Their experiments indicated that 50% of the patients treated with a large amount of lysozyme had improved immune ability as compared with the controls (Chemiother IV n.2:147–155, 1985). As to the mechanism of lysozyme inhibition on tumor, there are two possibilities: (1) lysozyme directly activates the organism's immunity functions; (2) lysozyme indirectly enhances the organism's immune ability (1989 Anticancer Research 9, 583–592).

Example 3

Expression of LYC3 in *E. coli*

The cDNA sequence encoding LYC3 was amplified with oligonucleotide PCR primers corresponding to 5'- and 3'-end of said DNA sequence, using human brain λ gt 11 cDNA library (Clontech) as a template. The resultant product was used as an insertion fragment.

The sequence of 5'-end oligonucleotide primer was:

5'-TCTCGGATCCATGTTGTTGGCCCTGGTCT-3' (SEQ ID NO: 5).

This primer contained a cleavage site of restriction endonuclease BamHI, followed by 19 nucleotides of LYC3 coding sequence starting from the start codon.

The sequence of 3'-end primer was:

5'-CCTTGTCGACCTAGAAGTCACAGCCATCC-3' (SEQ ID NO: 6).

This primer contains a cleavage site of restriction endonuclease SalI, a translation terminator and partial LYC3 coding sequence.

These cleavage sites of restriction endonuclease in primers corresponded to the cleavage sites in bacterial expression vector pQE-9 (Qiagen Inc., Chatsworth, Calif.). Vector pQE-9 encodes an antibiotic resistance (Amp$^r$), a bacterial replication origin (ori), an IPTG-adjustable promotor/operon (P/O), a ribosome-binding site (RBS), a six-hisitine tag (6-His) and cloning sites of restriction endonuclease.

Vector pQE-9 and insertion fragments were digested by BamHI and SalI, and then linked together, ensuring that the open reading frame started from the bacterial RBS. Then, the linkage mixture was used to transform *E.coli* M15/rep4 (Qiagen) containing multi-copy of plasmid pREP4 which expressed repressor of lacI and was resistant to kanamycin (Kan$^r$). Transformants were screened out in LB medium containing Amp and Kan. The positive clones of transformant were cultured overnight in LB liquid medium supplemented with Amp (100 ug/ml) and Kan (25 ug/ml). The plasmids were extracted. The size and direction of the inserted fragments were verified by HindIII digestion. The sequencing confirmed that LYC3 cDNA fragment was correctly inserted into the vector.

The overnight culture was 1:100–1:250 diluted, inoculated into large volume medium, and cultured until the 600 nm optical density ($OD_{600}$) reached 0.4–0.6. IPTG (isopropylthiobeta-D-galactoside) was added to final concentration of 1 mM. By deactivating repressor of LacI, IPTG induced and promoted P/O, thereby increasing the expression of gene. The cells were cultured for another 3–4 hours, and then centrifuged (6000×g, 20 mins). The cultures were sonicated, and cell lysate was collected and diluted with 6M guanidine hydrochloride. After clarification, the dissolved LYC3 in solution were purified by nickel-chelated column chromatography under the conditions suitable for the tight binding of 6-His tagged protein and column. LYC3 was eluted with 6M-guanidine hydrochloride (pH 5.0). The denaturalized proteins in guanidine hydrochloride were precipitated by several methods. First, guanidine hydrochloride was separated by dialysis. Alternatively, the purified protein, which was isolated from nickel-chelated column, bound to the second column with decreased linear gradient of guanidine hydrochloride. The proteins were denatured when binding to the column, and then eluted with guanidine hydrochloride (pH 5.0). Finally, the soluble proteins were dialyzed with PBS, then preserved in glycerol stock solution with the final glycerol concentration of 10% (w/v).

The molecular weight of the expressed protein was 16 kDa, as identified by 12% SDS-PAGE.

Moreover, the sequencing results of the 10 amino acids at the N- and C-terminal of the expressed protein indicated that they were identical to those in SEQ ID NO: 4.

Example 4

Expression of LYC3 in Eukaryotic Cells (CHO Cell Line)

In this example, the cDNA sequence encoding LYC3 was amplified with oligonucleotide PCR primers corresponding to 5'- and 3'-end of said DNA sequence, using human brain λ gt 11 cDNA library (Clontech) as a template. The resultant product was used as an insertion fragment.

The sequence of 5'-end oligonucleotide primer was:

5'-TCTCAAGCTTATGTTGTTGGCCCTGGTCT-3' (SEQ ID NO: 7),

This primer contained a cleavage site of restriction endonuclease HindIII, followed by 20 nucleotides of LYC3 coding sequence starting from the start codon.

The sequence of 3'-end primer was:

5'-CCTTGGATCCCTAGAAGTCACAGCCATCC-3' (SEQ ID NO: 8)

The primer contained a cleavage site of restriction endonuclease BamHI, a translation stop codon, and partial LYC3 coding sequence.

These cleavage sites of restriction endonuclease in primers corresponded to the cleavage sites in expression vector pcDNA3 for CHO cell. This vector encoded two kinds of antibiotic resistance (Amp$^r$ and Neo$^r$), a phage replication origin (f1 ori), a virus replication origin (SV40 ori), a T7 promoter, a virus promoter (P-CMV), a Sp6 promoter, a polyadenylation signal of SV40 and the corresponding poly A sequence thereof, a polyadenylation signal of BGH and the poly A sequence thereof.

The vector pcDNA3 and insertion fragment were digested with HindIII and BamHI, and linked together. Subsequently, *E.coli* strand DH5 α was transformed with linkage mixture.

Transformants were screened out in LB medium containing Amp. The clones containing the needed constructs were cultured overnight in LB liquid medium supplemented with Amp (100 ug/ml). Plasmids were extracted. The sequencing indicated that LYC3 cDNA fragment was correctly inserted into the vector.

Plasmids were transfected into CHO cells by lipofection with Lipofectin Kit (GIBco Life). After transfecting the cells for 48 hours and screening the cells with G418 for 2–3 weeks, the cells and cell supernatant were collected and the enzyme activity of the expressed protein was measured. G418 was removed and the transformants were subcultured continuously. The mixed clonal cells were limiting diluted and the subclones with higher protein activity were selected. The positive subclones were mass cultured by routine methods. 48 hours later, the cells and supernatant were collected. The cells were ultrasonicated. Using 50 mM Tris-HCl (pH7.6) solution containing 0.05% Triton as an equilibrium solution and eluent, the active peek of the protein was collected with a pre-balanced Superdex G-75 column. Then, using 50 mM Tris-HCl (pH8.0) solution containing 0–1 M NaCl as an eluent, the protein was gradiently washed on a DEAE-Sepharose column balanced with 50 mM Tris-HCl (pH8.0) solution. The active peek of the protein was collected. The solution of the expressed protein was dialyzed with PBS (pH7.4), and finally lyophilized and preserved.

The molecular weight of the expressed protein was 15 kDa as identified by 12% SDS-PAGE.

Meanwhile, a 5'-end oligonucleotide primer was designed to remove signal peptide: 5'-TCTCAAGCTTAAGC TCTACGGTCGTTG-3' (SEQ ID NO: 9). The above procedure of Example 4 was repeated except that SEQ ID NOs: 9 and 8 were used as primers. An expressed protein with the molecular weight of 15 kDa was obtained, which was LYC3 without the signal peptide.

Moreover, the sequencing results of the 10 amino acids at the N- and C-terminal of the expressed protein indicated that they were identical to those in SEQ ID NO: 4.

Example 5
Antibody Preparation

Antibodies were produced by immunizing animals with the recombinant proteins obtained in the above examples. The method was as follows: the recombinant proteins were isolated by chromatography, and stored for use. Alternatively, the protein was isolated by SDS-PAGE electrophoresis, and obtained by cutting eletrophoretic bands from gel. The protein was emulsified with Freund's complete adjuvant of the same volume. The emulsified protein was injected intraperitoneally into mice at a dosage of 50–100 ug/0.2 ml. 14 days later, the same antigen was emulsified with Freund's incomplete adjuvant and injected intraperitoneally into mice at a dosage of 50–100 ug/0.2 ml for booster immunization. Booster immunization was carried out every 14 days, for at least three times. The specific activity of the obtained antiserum was evaluated by its ability of precipitating the translation product of LYC3 gene in vitro.

Example 6
The Bacteriolysis Effect of LYC3

In the similar manner described in Example 3, the LYC3 gene was amplified using primer with EcoRI and primer with XhoI sites. Then, the LYC3 amplification product was digested by EcoRI and XhoI, and cloned into vector pPIC9K (Invitrogen). The vector was digested by SalI and transformed into *Pichia pastoris* by electroporation. The yeast in which LYC3 gene was incorporated was screened out on a His(−) medium.

The supernatant of the culture of *Pichia pastoris* incorporated with LYC3 was used as a sample, and diluted in serial in 1:1, 1:5, 1:10, 1:20; 1:30, and 1:50. The supernatant of the culture of *Pichia pastoris* not incorporated with LYC3 was used as a control. 100 ul of sample or control was preheated at 37° C. for 2 mins. The substrate (*Micrococcus lysodeikticus* marked with Red Dye K-2BP and suspended in 0.5 M phosphate buffer, pH 6.5) preheated at 37° C. was added and reacted at 37° C. for 20 mins. 400 Ul of emulsifier was added to stop the reaction. The reaction mixture was centrifugated 4000 rpm 5 mins and the supernatant was taken and observed by naked eye. The samples were redder than the control. The reaction liquid was read on a Model 721 spectrophotometer at 540 wave length and a blank tube was used as a control. The absorbance of the sample were larger than that of the control. See FIG. 2A. On the top were the lysozyme products commercially available from Sigma. From left to right were $10^{-2}$, $5\times10^{-3}$, $2\times10^{-3}$, $5\times10^{-4}$, and $10^{-4}$ mg lysozyme and the control. Below were the culture supernatants of LYC3 protein of the invention, and from left to right were 1:1, 1:5, 1:10, 1:20; 1:30, and 1:50 diluted LYC3 supernatant, and the control. The deeper red color indicated that more bacteria were lysed. LYC3 had bacteriolysis effect as shown in FIG. 2A.

All the documents cited herein are incorporated into the invention as reference, as if each of them is individually incorporated. Further, it is appreciated that, in the above teaching of the invention, the skilled in the art can make certain changes or modifications to the invention, and these equivalents are still within the scope of the invention defined by the appended claims of the present application.

What is claimed is:

1. An isolated DNA molecule comprising a nucleotide sequence encoding a protein comprising the amino acid sequence of SEQ ID NO:4, wherein said protein has lysozyme activity.

2. The DNA molecule of claim 1 wherein said nucleotide sequence comprises the nucleotide sequence of nucleotides 81–521 of SEQ ID NO:3.

3. A vector containing the DNA sequence of claim 1.

4. A host cell transformed by the vector of claim 3.

5. The host cell of claim 4 which is *E. coli*.

6. The host cell of claim 4 which is a eukaryotic cell.

7. A method for producing an LYC3 protein having lysozyme-activity comprising:

(a) introducing an expression vector for production of LYC3 protein, said vector comprising a nucleotide sequence encoding a protein having the amino acid sequence of SEQ ID NO:4 or of amino acids 19–146 of SEQ ID NO:4, wherein said nucleotide sequence is operably linked to at least one expression control sequence, into a host cell, thereby forming a recombinant host cell;

(b) culturing the recombinant host cell of (a) under conditions suitable for expression of the DNA molecule encoding the protein, such that LYC3 protein is produced; and (c) isolating the LYC3 protein so produced, wherein said nucleotide sequence comprises nucleotides 81–521 of SEQ ID NO:3.

8. An isolated LYC3 protein having lysozyme activity comprising a polypeptide having an amino acid sequence selected from the group consisting of SEQ ID NO:4 and amino acids 19–146 of SEQ ID NO:4.

9. An isolated DNA molecule having a nucleotide sequence encoding a lysozyme consisting of the amino acid sequence of amino acids 19–146 of SEQ ID NO:4, wherein said lysozyme has lysozyme activity.

\* \* \* \* \*

SEQUENCE LISTING

<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 1
agagtggtgg tggctccact ctg                    23

```
<210> SEQ ID NO 2
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 2
tgctgtgcat ggttccgtcc atc                                              23

<210> SEQ ID NO 3
<211> LENGTH: 544
<212> TYPE: DNA
<213> ORGANISM: Human
<220> FEATURE:
<221> NAME/KEY: CDS
<222> LOCATION: (81)...(521)
<223> OTHER INFORMATION: Lysozyme LYCH3

<400> SEQUENCE: 3
agagtggtgg tggctccact ctgccgccgc atagaagcca ggagcagggc tctcagaagg      60
cggtggtgcc agctgggatc atg ttg ttg gcc ctg gtc tgt ctg ctc agc tgc    113
                      Met Leu Leu Ala Leu Val Cys Leu Leu Ser Cys
                        1               5                  10 ctg cta ccc tcc agt gag gcc aag ctc tac ggt cgt tgt gaa ctg gcc      161
Leu Leu Pro Ser Ser Glu Ala Lys Leu Tyr Gly Arg Cys Glu Leu Ala
            15                  20                  25 aga gtg cta cat gac ttc ggg ctg gac gga tac cgg gga tac agc ctg      209
Arg Val Leu His Asp Phe Gly Leu Asp Gly Tyr Arg Gly Tyr Ser Leu
         30                  35                  40 gct gac tgg gtc tgc ctt gct tat ttc aca agc ggt ttc aac gca gct      257
Ala Asp Trp Val Cys Leu Ala Tyr Phe Thr Ser Gly Phe Asn Ala Ala
     45                  50                  55 gct ttg gac tac gag gct gat ggg agc acc aac aac ggg atc ttc cag      305
Ala Leu Asp Tyr Glu Ala Asp Gly Ser Thr Asn Asn Gly Ile Phe Gln
 60                  65                  70                  75 atc aac agc cgg agg tgg tgc agc aac ctc acc ccg aac gtc ccc aac      353
Ile Asn Ser Arg Arg Trp Cys Ser Asn Leu Thr Pro Asn Val Pro Asn
                 80                  85                  90 gtg tgc cgg atg tac tgc tca gat ttg ttg aat cct aat ctc aag gat      401
Val Cys Arg Met Tyr Cys Ser Asp Leu Leu Asn Pro Asn Leu Lys Asp
             95                 100                 105 acc gtt atc tgt gcc atg aag ata acc caa gag cct cag ggt ctg ggt      449
Thr Val Ile Cys Ala Met Lys Ile Thr Gln Glu Pro Gln Gly Leu Gly
         110                 115                 120 tac tgg gag gcc tgg agg cat cac tgc cag gga aaa gac ctc act gaa      497
Tyr Trp Glu Ala Trp Arg His His Cys Gln Gly Lys Asp Leu Thr Glu
     125                 130                 135 tgg gtg gat ggc tgt gac ttc tag gatggacgga accatgcaca gca             544
Trp Val Asp Gly Cys Asp Phe  *
140                 145

<210> SEQ ID NO 4
<211> LENGTH: 146
<212> TYPE: PRT
<213> ORGANISM: Human

<400> SEQUENCE: 4

Met Leu Leu Ala Leu Val Cys Leu Leu Ser Cys Leu Leu Pro Ser Ser
  1               5                  10                  15

Glu Ala Lys Leu Tyr Gly Arg Cys Glu Leu Ala Arg Val Leu His Asp
             20                  25                  30
```

Phe Gly Leu Asp Gly Tyr Arg Gly Tyr Ser Leu Ala Asp Trp Val Cys
            35                  40                  45

Leu Ala Tyr Phe Thr Ser Gly Phe Asn Ala Ala Ala Leu Asp Tyr Glu
    50                  55                  60

Ala Asp Gly Ser Thr Asn Asn Gly Ile Phe Gln Ile Asn Ser Arg Arg
65                  70                  75                  80

Trp Cys Ser Asn Leu Thr Pro Asn Val Pro Asn Val Cys Arg Met Tyr
                85                  90                  95

Cys Ser Asp Leu Leu Asn Pro Asn Leu Lys Asp Thr Val Ile Cys Ala
            100                 105                 110

Met Lys Ile Thr Gln Glu Pro Gln Gly Leu Gly Tyr Trp Glu Ala Trp
            115                 120                 125

Arg His His Cys Gln Gly Lys Asp Leu Thr Glu Trp Val Asp Gly Cys
        130                 135                 140

Asp Phe
145

<210> SEQ ID NO 5
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 5
tctcggatcc atgttgttgg ccctggtct                                    29

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 6
ccttgtcgac ctagaagtca cagccatcc                                    29

<210> SEQ ID NO 7
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 7
tctcaagctt atgttgttgg ccctggtct                                    29

<210> SEQ ID NO 8
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 8
ccttggatcc ctagaagtca cagccatcc                                    29

<210> SEQ ID NO 9
<211> LENGTH: 27
<212> TYPE: DNA
<213> ORGANISM: Artificial Sequence
<220> FEATURE:

```
<223> OTHER INFORMATION: Oligonucleotide primer

<400> SEQUENCE: 9
tctcaagctt aagctctacg gtcgttg                                     27

<210> SEQ ID NO 10
<211> LENGTH: 19
<212> TYPE: PRT
<213> ORGANISM: Artificial Sequence
<220> FEATURE:
<223> OTHER INFORMATION: Signature sequence of lysozyme and
      alpha-lactoalbumin
<221> NAME/KEY: VARIANT
<222> LOCATION: (2)...(4)
<223> OTHER INFORMATION: Any amino acid
<221> NAME/KEY: VARIANT
<222> LOCATION: (6)...(7)
<223> OTHER INFORMATION: Any amino acid
<221> NAME/KEY: VARIANT
<222> LOCATION: (8)...(8)
<223> OTHER INFORMATION: Leucine, methionine or phenylalanine
<221> NAME/KEY: VARIANT
<222> LOCATION: (9)...(11)
<223> OTHER INFORMATION: Any amino acid
<221> NAME/KEY: VARIANT
<222> LOCATION: (12)...(12)
<223> OTHER INFORMATION: Aspartate, glutamate or asparagine
<221> NAME/KEY: VARIANT
<222> LOCATION: (13)...(13)
<223> OTHER INFORMATION: Leucine or isoleucine
<221> NAME/KEY: VARIANT
<222> LOCATION: (14)...(18)
<223> OTHER INFORMATION: Any amino acid

<400> SEQUENCE: 10

Cys Xaa Xaa Xaa Cys Xaa Xaa Xaa Xaa Xaa Xaa Xaa Xaa Xaa Xaa
 1               5                  10                 15

Xaa Xaa Cys

<210> SEQ ID NO 11
<211> LENGTH: 148
<212> TYPE: PRT
<213> ORGANISM: Trachypithecus francoisi

<400> SEQUENCE: 11

Met Arg Ala Leu Ile Ile Leu Gly Leu Val Leu Leu Ser Val Thr Val
 1               5                  10                  15

Gln Gly Lys Ile Phe Glu Arg Cys Glu Leu Ala Arg Thr Leu Lys Lys
            20                  25                  30

Leu Gly Leu Asp Gly Tyr Lys Gly Val Ser Leu Ala Asn Trp Val Cys
        35                  40                  45

Leu Ala Lys Trp Glu Ser Gly Tyr Asn Thr Glu Ala Thr Asn Tyr Asn
    50                  55                  60

Pro Gly Asp Glu Ser Thr Asp Tyr Gly Ile Phe Gln Ile Asn Ser Arg
65                  70                  75                  80

Tyr Trp Cys Asn Asn Gly Lys Thr Pro Gly Ala Val Asp Ala Cys His
                85                  90                  95

Ile Ser Cys Ser Ala Leu Leu Gln Asn Asn Ile Ala Asp Ala Val Ala
            100                 105                 110

Cys Ala Lys Arg Val Val Ser Asp Pro Gln Gly Ile Arg Ala Trp Val
        115                 120                 125

Ala Trp Arg Asn His Cys Gln Asn Lys Asp Val Ser Gln Tyr Val Lys
    130                 135                 140

Gly Cys Gly Val
```

```
145

<210> SEQ ID NO 12
<211> LENGTH: 147
<212> TYPE: PRT
<213> ORGANISM: Ring-necked pheasant

<400> SEQUENCE: 12

Met Arg Ser Leu Leu Ile Leu Val Leu Cys Phe Leu Pro Leu Ala Ala
1               5                   10                  15

Pro Gly Lys Val Tyr Gly Arg Cys Glu Leu Ala Ala Ala Met Lys Arg
            20                  25                  30

Met Gly Leu Asp Asn Tyr Arg Gly Tyr Ser Leu Gly Asn Trp Val Cys
        35                  40                  45

Ala Ala Lys Phe Glu Ser Asn Phe Asn Thr Gly Ala Thr Asn Arg Asn
50                  55                  60

Thr Asp Gly Ser Thr Asp Tyr Gly Ile Leu Gln Ile Asn Ser Arg Trp
65                  70                  75                  80

Trp Cys Asn Asp Gly Arg Thr Pro Gly Ser Lys Asn Leu Cys His Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Lys His Cys Lys Gly Thr Asp Val Asn Val Trp Ile Arg Gly
    130                 135                 140

Cys Arg Leu
145
```